United States Patent
Jin et al.

(10) Patent No.: US 11,642,608 B2
(45) Date of Patent: May 9, 2023

(54) METHOD OF PREPARING HOVENIA DULCIS THUNB EXTRACT RICH IN DIHYDROMYRICETIN

(71) Applicants: Ziheng Jin, Luohe (CN); Sujing Gu, Luohe (CN); Yanjun Wen, Luohe (CN); Linzheng Li, Luohe (CN)

(72) Inventors: Ziheng Jin, Luohe (CN); Sujing Gu, Luohe (CN); Yanjun Wen, Luohe (CN); Linzheng Li, Luohe (CN)

(73) Assignee: HENAN ZHONGDA HENGYUAN BIOTECHNOLOGY STOCK CO., LTD., Henan (CN)

( * ) Notice: Subject to any disclaimer, the term of this patent is extended or adjusted under 35 U.S.C. 154(b) by 124 days.

(21) Appl. No.: 17/346,329

(22) Filed: Jun. 14, 2021

(65) Prior Publication Data
US 2021/0402323 A1 Dec. 30, 2021

(30) Foreign Application Priority Data
Jun. 30, 2020 (CN) .......................... 202010616851.4

(51) Int. Cl.
| | | |
|---|---|---|
| B01D 11/02 | (2006.01) | |
| B01D 21/26 | (2006.01) | |
| B01D 37/00 | (2006.01) | |
| A61K 36/48 | (2006.01) | |
| B01D 11/04 | (2006.01) | |
| A61K 36/482 | (2006.01) | |
| C07D 311/28 | (2006.01) | |

(52) U.S. Cl.
CPC ........ *B01D 11/0288* (2013.01); *A61K 36/482* (2013.01); *B01D 11/0292* (2013.01); *B01D 11/048* (2013.01); *B01D 21/262* (2013.01); *B01D 37/00* (2013.01); *A61K 2236/33* (2013.01); *A61K 2236/51* (2013.01); *A61K 2236/53* (2013.01); *C07D 311/28* (2013.01)

(58) Field of Classification Search
CPC ............ B01D 11/0288; B01D 11/0292; B01D 11/048; B01D 11/0257; B01D 11/0296; B01D 21/26; B01D 21/262; B01D 36/00; B01D 36/045; B01D 37/00; B01D 25/12; B01D 25/127; B01D 25/21; B01D 63/08; B01D 63/0822; C07D 311/28; A61K 36/72; A61K 31/352; A61K 2236/333; A61K 2236/51; A61K 2236/53; A61K 36/00; A61K 36/48; A61K 36/482; A61K 2236/15; A61K 2236/33; A61K 2236/39; A61K 2236/50; A61K 2236/55; A23L 2/38; A23L 33/105
See application file for complete search history.

(56) References Cited

U.S. PATENT DOCUMENTS

| | | | | |
|---|---|---|---|---|
| 2004/0058016 A1* | 3/2004 | Na | ............................ | A61P 1/16 536/123 |
| 2007/0160699 A1* | 7/2007 | Kim | ...................... | A23L 33/105 424/769 |
| 2017/0014461 A1* | 1/2017 | Jia | ............................. | A61P 1/16 |
| 2018/0338513 A1* | 11/2018 | Lian | ........................ | C09B 61/00 |

FOREIGN PATENT DOCUMENTS

| | | | | |
|---|---|---|---|---|
| CN | 101007797 A | * | 8/2007 | ........... C07D 311/32 |
| CN | 101336987 A | * | 1/2009 | ............. A61Q 19/00 |
| CN | 101390979 A | | 3/2009 | |
| CN | 201455354 A | * | 6/2009 | ........... A61K 36/076 |
| CN | 109170398 A | * | 1/2019 | ............. A23L 31/00 |
| CN | 109601789 A | | 4/2019 | |
| CN | 110201012 A | * | 9/2019 | .............. A61P 17/00 |

OTHER PUBLICATIONS

Guo et al, Translated Abstract of Document CN109170398A, published Jan. 11, 2019. (Year: 2019).*
Lin et al, Translated abstract of Document CN201455354A, published Jun. 17, 2009. (Year: 2009).*
Zhang et al, Translated abstractor Document CN101007797A, published Aug. 1, 2007. (Year: 2007).*
Zhang et al, Translated abstract of Document CN101336987, published Jan. 7, 2009. (Year: 2009).*
Yuan et al, Translated Abstract of Document CN110201012, published Sep. 6, 2019 (Year: 2019).*
Seung Mi Yoo et al, "Recovery and pre-purification of (+)-dihydromyricetin from Hovenia dulcis", published in Process Biochemistry, vol. 4, 2006, pp. 567-570. (Year: 2006).*
Patricia Morales et al, "Hovenia dulcis Thunb. pseudofruits as functional foods: Phytochemicals and bioactive properties in different maturity stages", published in Journal of Functional Foods, vol. 29, 2017, pp. 37-45. (Year: 2017).*

* cited by examiner

Primary Examiner — Joseph W Drodge

(57) ABSTRACT

A method for preparing a *Hovenia dulcis* Thunb extract rich in dihydromyricetin includes the following steps: (1) crushing *Hovenia dulcis* Thunb seeds to obtain a *Hovenia dulcis* Thunb powder; (2) adding a 10-95% ethanol solution in an amount of 3-15 times of an amount of the *Hovenia dulcis* Thunb powder, stirring and extracting at 20° C.-80° C. twice; (3) filtering to obtain an extract solution; (4) concentrating the extract solution by evaporating ethanol under reduced pressure to obtain a crude extract, the crude extract having a solid content of 10%-40%; (5) placing the crude extract at −20° C. to 8° C. for 0.5 to 12 hours; (6) centrifuging the crude extract to obtain a supernatant; and (7) spray-drying the supernatant to obtain the *Hovenia dulcis* Thunb extract.

12 Claims, No Drawings

METHOD OF PREPARING HOVENIA DULCIS THUNB EXTRACT RICH IN DIHYDROMYRICETIN

This application claims priority to Chinese Patent Application No. 202010616851.4, filed on Jun. 30, 2020, which is incorporated by reference for all purposes as if fully set forth herein.

TECHNICAL FIELD

The invention relates to the preparation of medicinal and food raw materials, and in particular, relates to a method for extracting and preparing effective ingredients, more specifically, a method for preparing a *Hovenia dulcis* Thunb extract rich in dihydromyricetin.

TECHNICAL BACKGROUND

*Hovenia dulcis* Thunb extract is the extract of the dried mature seeds of *Hovenia dulcis* Thunb, a plant of the Rhamnaceae family. It is included in the "Medicine Standards of the Ministry of Health of People's Republic of China: Chinese Medicinal Materials." It is listed as both food and medicine. It has the effects of clearing heat, diuresis, and anti-alcoholic toxins. It is mainly used to treat alcoholic diseases, irritability, thirst, vomiting, diarrhea and other diseases. *Hovenia dulcis* Thunb extract contains flavonoid active ingredients kaempferol, apigenin, myricetin, quercetin, hydromyricetin and anthraquinone compound emodin. Among them, the content of dihydromyricetin is relatively high. Dihydromyricetin has liver protection, anti-inflammatory, analgesic, lowering blood lipids, increasing SOD activity, antibacterial, antiviral and other pharmacological effects. The market's requirements for *Hovenia dulcis* Thunb extract are not limited to the content of flavonoids, but also the content of dihydromyricetin.

At present, the extraction process of *Hovenia dulcis* Thunb extract mainly uses hot water extraction, low-grade alcohol extraction, or acid-base extraction, but the extracts obtained by these methods have low dihydromyricetin content or poor solubility in water, which is difficult to meet the requirements of beverage and food industry. CN 109601789A discloses a method of preparing high-clarity water-soluble *Hovenia dulcis* Thunb extract. The method uses flavonoids as an indicator, extracting with deionized water, filtering while hot, centrifuging, and then concentrating under a vacuum to obtain a solid and crushing to obtain an extract powder. The method uses water extraction with a total flavonoid content of 10%, a recovery rate of about 60%, a low total flavonoid yield and content, resulting in waste of raw materials, and vacuum concentration, crushing and drying process has high energy consumption and complicated operation. CN 200810226063.3 discloses an extract of *Hovenia dulcis* and its preparation method and application in the preparation of antitumor drugs. The method uses water and/or organic solvents extract from *Hovenia dulcis*. The organic solvent used is methanol, ethanol, petroleum ether, chloroform, dichloromethane, ethyl acetate, n-butanol, benzene or toluene. The method not only uses a large amount of organic solvents and has high cost and complex process, but also results in *Hovenia dulcis* extract having poor water solubility, aturbid aqueous solution, which cannot be directly applied to the food and beverage industry.

SUMMARY OF THE INVENTION

In order to overcome the shortcomings described in the background art, the purpose of the present invention is to solve the problem of the solubility of *Hovenia dulcis* Thunb extract in food, and to provide an easy to operate, low-cost preparation method to prepare a water-soluble extract rich in dihydromyricetin.

The present invention provides a method for preparing a *Hovenia dulcis* Thunb extract rich in dihydromyricetin, and the method includes the following steps:

(1) crushing *Hovenia dulcis* Thunb seeds to obtain a *Hovenia dulcis* Thunb powder;

(2) adding a 10-95% ethanol solution in an amount of 3-15 times of an amount of the *Hovenia dulcis* Thunb powder, stirring and extracting at 20° C.-80° C. twice;

(3) filtering to obtain an extract solution;

(4) concentrating the extract solution by evaporating ethanol under reduced pressure to obtain a crude extract, the crude extract having a solid content of 10%-40%;

(5) placing the crude extract at −20° C. to 8° C. for 0.5 to 12 hours;

(6) centrifuging the crude extract to obtain a supernatant; and (7) spray-drying the supernatant to obtain the *Hovenia dulcis* Thunb extract.

Preferably, in step (1), the *Hovenia dulcis* Thunb seeds are dried *Hovenia dulcis* Thunb seeds, and are crushed and passed through a 20 mesh screen.

Preferably, in step (2), a 30-85% ethanol solution is added in an amount of 3-12 times of the amount of the *Hovenia dulcis* Thunb powder; and the 30-85% ethanol solution and the *Hovenia dulcis* Thunb powder are stirred and extracted at 20-70° C. for 1-4 hours.

Preferably, in step (2), a 70% ethanol solution is added in an amount of 6 times of the amount of the *Hovenia dulcis* Thunb powder; and the 70% ethanol solution and the *Hovenia dulcis* Thunb powder are stirred and extracted at 60° C. for 1 hour twice.

Preferably, in step (3), the extract is subjected to a plate and frame filtration.

Preferably, in the step (4), rotary evaporation is used to remove ethanol at 60-80° C. under a vacuum of 0.06-0.095 Mpa; the crude extract has a solid content of 25%.

Preferably, in the step (5), the crude extract is placed at 0° C. for 3 hours.

Preferably, in the step (6), the crude extract is centrifuged at a centrifugation rate of 2000-5000 r/min.

Preferably, in the step (6), the crude extract is centrifuged at a centrifugation rate of 3000 r/min for 10 minutes.

Preferably, the *Hovenia dulcis* Thunb extract has a dihydromyricetin extraction rate of 82.6% and a dihydromyricetin content of 12.2%.

The present invention also provides another method for preparing a *Hovenia dulcis* Thunb extract rich in dihydromyricetin, and the method includes the following steps:

(1) crushing 1 kg of *Hovenia dulcis* Thunb seeds and passing through a 20 mesh screen to obtain a *Hovenia dulcis* Thunb powder;

(2) adding 6 kg of 70% ethanol solution to the *Hovenia dulcis* Thunb powder, stirring and extracting at 60° C. for 1 hour twice;

(3) filtering to obtain an extract solution via a plate and frame filtration;

(4) concentrating the extract solution by evaporating ethanol under reduced pressure to obtain a crude extract, the crude extract having a solid content of 25%;

(5) placing the crude extract at 0° C. for 3 hours;

(6) centrifuging the crude extract at a centrifugation rate of 3000 r/min for 10 minutes to obtain a supernatant; and (7) spray-drying the supernatant to obtain the *Hovenia dulcis* Thunb extract.

Preferably, the *Hovenia dulcis* Thunb extract has a dihydromyricetin extraction rate of 82.6% and a dihydromyricetin content of 12.2%.

The content of the dihydromyricetin of the *Hovenia dulcis* Thunb extract is as high as 10%. At the same time, the product has good water solubility and the aqueous solution is clear and translucent. Compared with the existing *Hovenia dulcis* extract, the turbidity is low and the content of dihydromyricetin is high, which increases its practicality in food and health products and expands its application. range. The method of the invention is convenient and simple to operate, and can meet the needs of large-scale industrial production.

DETAILED DESCRIPTION

Example 1

Taking 1 kg of *Hovenia dulcis* Thunb seeds, crushing them into coarse powder, passing through a 20 mesh sieve, adding 6 kg of 70% ethanol, stirring and extracting at 60° C. 2 times, 1 h each time, combining the extracts, filtering by a plate and frame filtration, and recovering ethanol under reduced pressure. A crude extract solution with a solid content of 25% was obtained, and the crude extract was refrigerated to stand at 0° C. for 3 h, centrifuged at 3000 r/min for 10 minutes, and the supernatant was collected and directly spray-dried to obtain 94.8 g of *Hovenia dulcis* Thunb extract. The dihydromyricetin extraction rate was 82.6%, the dihydromyricetin content was 12.2%, the 2% aqueous solution of the extract was clear and translucent, and the turbidity was 0.8 NTU.

Example 2

Taking 1 kg of *Hovenia dulcis* Thunb seeds, crushing them into coarse powder, passing through a 20 mesh sieve, adding 6 kg of 70% ethanol, stirring and extracting at 60° C. 2 times, 1 h each time, combining the extracts, filtering by a plate and frame filtration, and recovering ethanol under reduced pressure. A crude extract solution with a solid content of 45% was obtained, and the crude extract was refrigerated to stand at 0° C. for 3 h, centrifuged at 3000 r/min for 10 minutes, and the supernatant was collected and directly spray-dried to obtain 166 g of *Hovenia dulcis* Thunb extract. The dihydromyricetin extraction rate was 80.7%, the dihydromyricetin content was 6.8%, and the 2% aqueous solution of the extract had a large amount of precipitates.

Example 3

Taking 1 kg of *Hovenia dulcis* Thunb seeds, crushing them into coarse powder, passing through a 20 mesh sieve, adding 6 kg of 30% ethanol, stirring and extracting at 60° C. 2 times, 1 h each time, combining the extracts, filtering by a plate and frame filtration, and recovering ethanol under reduced pressure. A crude extract solution with a solid content of 45% was obtained, and the crude extract was refrigerated to stand at 0° C. for 12 h, centrifuged at 3000 r/min for 10 minutes, and the supernatant was collected and directly spray-dried to obtain 163 g of *Hovenia dulcis* Thunb extract. The dihydromyricetin extraction rate was 67.6%, the dihydromyricetin content was 5.8%, the 2% aqueous solution of the extract was turbid, and the turbidity was 54 NTU.

Comparative Example

Taking 1 kg of *Hovenia dulcis* Thunb seeds, crushing them into coarse powder, passing through a 20 mesh sieve, adding 6 kg of 95% ethanol, stirring and extracting at 60° C. 2 times, 1 h each time, combining the extracts, filtering by a plate and frame filtration, recovering ethanol under reduced pressure, and vacuum-drying to constant weight to obtain 123 g of *Hovenia dulcis* Thunb extract. The dihydromyricetin extraction rate was 24.2%, the dihydromyricetin content was 2.7%, the 2% aqueous solution of the extract was turbid, and there were a lot of floating substrates and precipitations.

The comparison results between the present invention and CN10390979 products are shown in the following table:

| *Hovenia dulcis* Thunb extract | Dihydromyricetin extraction rate % | 2% aqueous solution turbidity (NTU) |
| --- | --- | --- |
| Example 1 | 82.6 | 0.8 |
| Example 2 | 80.7 | Precipitates |
| Example 3 | 67.6 | 54 |
| CN 10390979 Product | 24.2 | Floating substrates, turbid solution, precipitates |

It can be seen that the *Hovenia dulcis* Thunb extract obtained by the present invention has excellent water solubility, high dihydromyricetin content and high yield, and can be used in food, beverages and oral liquids. The process operation is simple and feasible, and is suitable for industrial production.

Finally, it should be noted that obviously, the above-mentioned embodiments are merely examples for clearly illustrating the present invention, rather than limiting the implementation manners. For those of ordinary skill in the art, other changes or changes in different forms can be made on the basis of the above description. There is no need and cannot give an exhaustive list of all implementation methods. The obvious changes or changes derived from this are still within the protection scope of the present invention.

The invention claimed is:

1. A method for preparing a *Hovenia dulcis* Thunb extract rich in dihydromyricetin, consisting of the following steps:
   (1) crushing *Hovenia dulcis* Thunb seeds to obtain a *Hovenia dulcis* Thunb powder;
   (2) adding a 10-95% ethanol solution in an amount of 3-15 times of an amount of the *Hovenia dulcis* Thunb powder, stirring and extracting at 20° C.-80° C.;
   (3) filtering to obtain an extract solution;
   (4) concentrating the extract solution by evaporating ethanol under reduced pressure to obtain a crude extract, the crude extract having a solid content of 10%-40%;
   (5) placing the crude extract at −20° C. to 8° C. for 0.5 to 12 hours;
   (6) centrifuging the crude extract to obtain a supernatant; and
   (7) spray-drying the supernatant to obtain the *Hovenia dulcis* Thunb extract.

2. The method according to claim 1, wherein, in step (1), the *Hovenia dulcis* Thunb seeds are dried *Hovenia dulcis* Thunb seeds, and are crushed and passed through a 20 mesh screen.

3. The method according to claim 1, wherein in step (2), a 30-85% ethanol solution is added in an amount of 3-12 times of the amount of the *Hovenia dulcis* Thunb powder;

and the 30-85% ethanol solution and the *Hovenia dulcis* Thunb powder are stirred and extracted at 20-70° C. for 1-4 hours.

4. The method according to claim 3, wherein in step (2), a 70% ethanol solution is added in an amount of 6 times of the amount of the *Hovenia dulcis* Thunb powder; and the 70% ethanol solution and the *Hovenia dulcis* Thunb powder are stirred and extracted at 60° C. for 1 hour.

5. The method according to claim 1, wherein in step (3), the extract is subjected to a plate and frame filtration.

6. The method according to claim 1, wherein in the step (4), rotary evaporation is used to remove ethanol at 60-80° C. under a vacuum of 0.06-0.095 Mpa; the crude extract having a solid content of 25%.

7. The method according to claim 1, wherein in the step (5), the crude extract is placed at 0° C. for 3 hours.

8. The method according to claim 1, wherein in the step (6), the crude extract is centrifuged at a centrifugation rate of 2000-5000 r/min.

9. The method according to claim 8, wherein in the step (6), the crude extract is centrifuged at a centrifugation rate of 3000 r/min for 10 minutes.

10. The method according to claim 1, wherein the *Hovenia dulcis* Thunb extract has a dihydromyricetin extraction rate of 82.6% and a dihydromyricetin content of 12.2%.

11. A method for preparing a *Hovenia dulcis* Thunb extract rich in dihydromyricetin, consisting of the following steps:
(1) crushing 1 kg of *Hovenia dulcis* Thunb seeds and passing through a 20 mesh screen to obtain a *Hovenia dulcis* Thunb powder;
(2) adding 6 kg of 70% ethanol solution to the *Hovenia dulcis* Thunb powder, stirring and extracting at 60° C. for 1 hour;
(3) filtering to obtain an extract solution via a plate and frame filtration;
(4) concentrating the extract solution by evaporating ethanol under reduced pressure to obtain a crude extract, the crude extract having a solid content of 25%;
(5) placing the crude extract at 0° C. for 3 hours;
(6) centrifuging the crude extract at a centrifugation rate of 3000 r/min for 10 minutes to obtain a supernatant; and
(7) spray-drying the supernatant to obtain the *Hovenia dulcis* Thunb extract.

12. The method according to claim 11, wherein the *Hovenia dulcis* Thunb extract has a dihydromyricetin extraction rate of 82.6% and a dihydromyricetin content of 12.2%.

\* \* \* \* \*